(12) United States Patent
Popescu

(10) Patent No.: US 7,254,210 B2
(45) Date of Patent: Aug. 7, 2007

(54) MULTI-SLICE COMPUTER TOMOGRAPHY SYSTEM WITH DATA TRANSFER SYSTEM WITH REDUCED TRANSFER BANDWIDTH

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 113 days.

(21) Appl. No.: 11/109,324

(22) Filed: Apr. 19, 2005

(65) Prior Publication Data
US 2005/0238137 A1 Oct. 27, 2005

(30) Foreign Application Priority Data
Apr. 22, 2004 (DE) .................... 10 2004 019 599

(51) Int. Cl.
G01N 23/083 (2006.01)
(52) U.S. Cl. ....................................................... 378/19
(58) Field of Classification Search .................... 378/19
See application file for complete search history.

(56) References Cited

U.S. PATENT DOCUMENTS 4,494,141 A * 1/1985 Altekruse .................... 378/19
5,857,007 A 1/1999 Haq
6,205,199 B1 * 3/2001 Polichar et al. ............. 378/98.8
6,560,307 B2 * 5/2003 Marume ......................... 378/4
6,842,502 B2 * 1/2005 Jaffray et al. ................. 378/65
6,879,656 B2 * 4/2005 Cesmeli et al. ................. 378/4

FOREIGN PATENT DOCUMENTS
EP 1 061 476 6/2000

* cited by examiner

Primary Examiner—Edward J. Glick
Assistant Examiner—Thomas R. Artman
(74) Attorney, Agent, or Firm—Schiff Hardin LLP

(57) ABSTRACT

A computed tomography system has a stationary part and a part that is rotatable around an examination axis that carries at least one x-ray source, a detector unit opposite the x-ray source and a data acquisition unit connected to the detector unit. A data transfer device for transfer of measurement data (acquired with the data acquisition unit) to an image reconstruction device connected with the stationary part is disposed between the stationary part and the rotatable part. The rotatable part has a storage unit for buffering at least a part of the measurement data acquired with the data acquisition unit before their transfer. This storage unit is connected to the data acquisition unit. The computed tomography system enables operation with a high data rate without the data transfer device having to adapt to the maximal data rate.

13 Claims, 2 Drawing Sheets

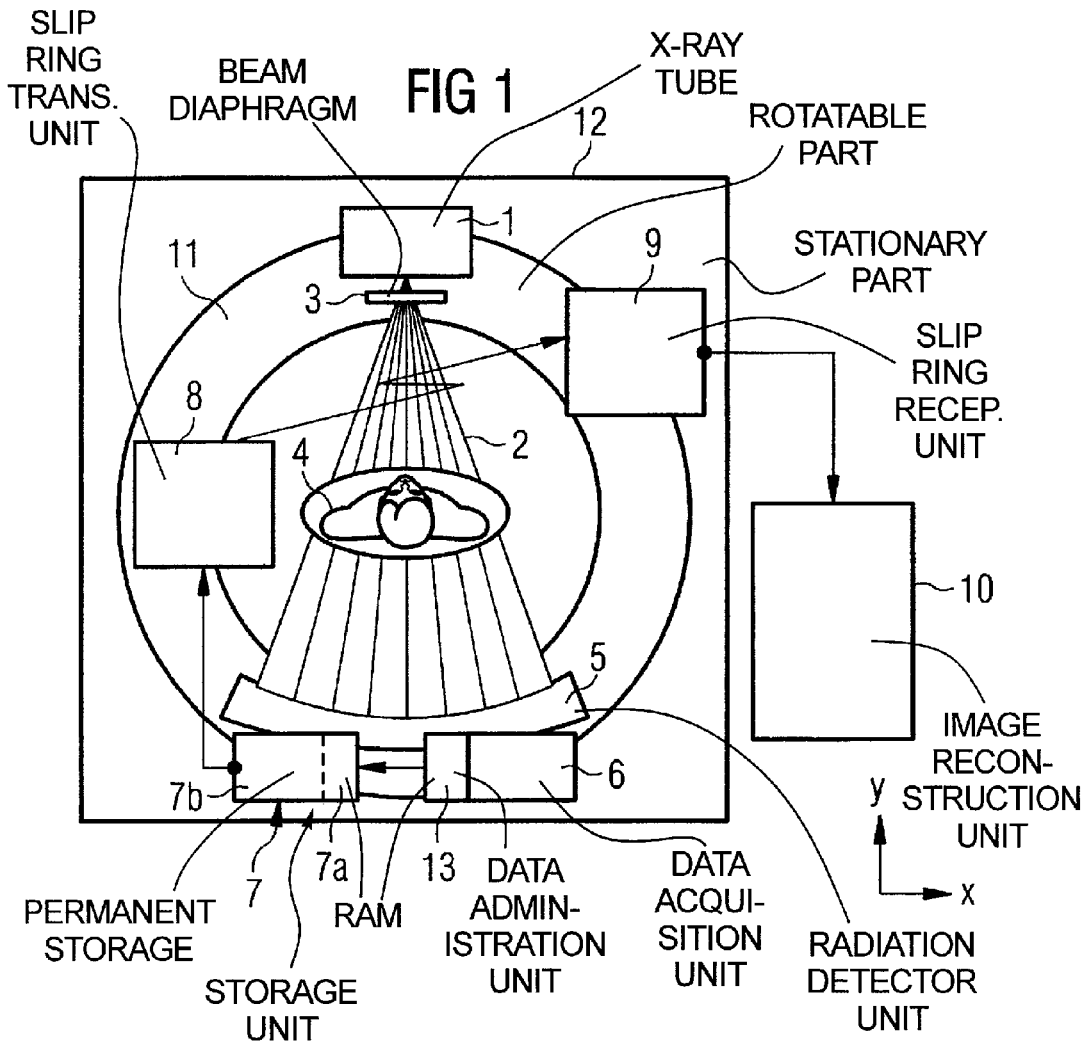

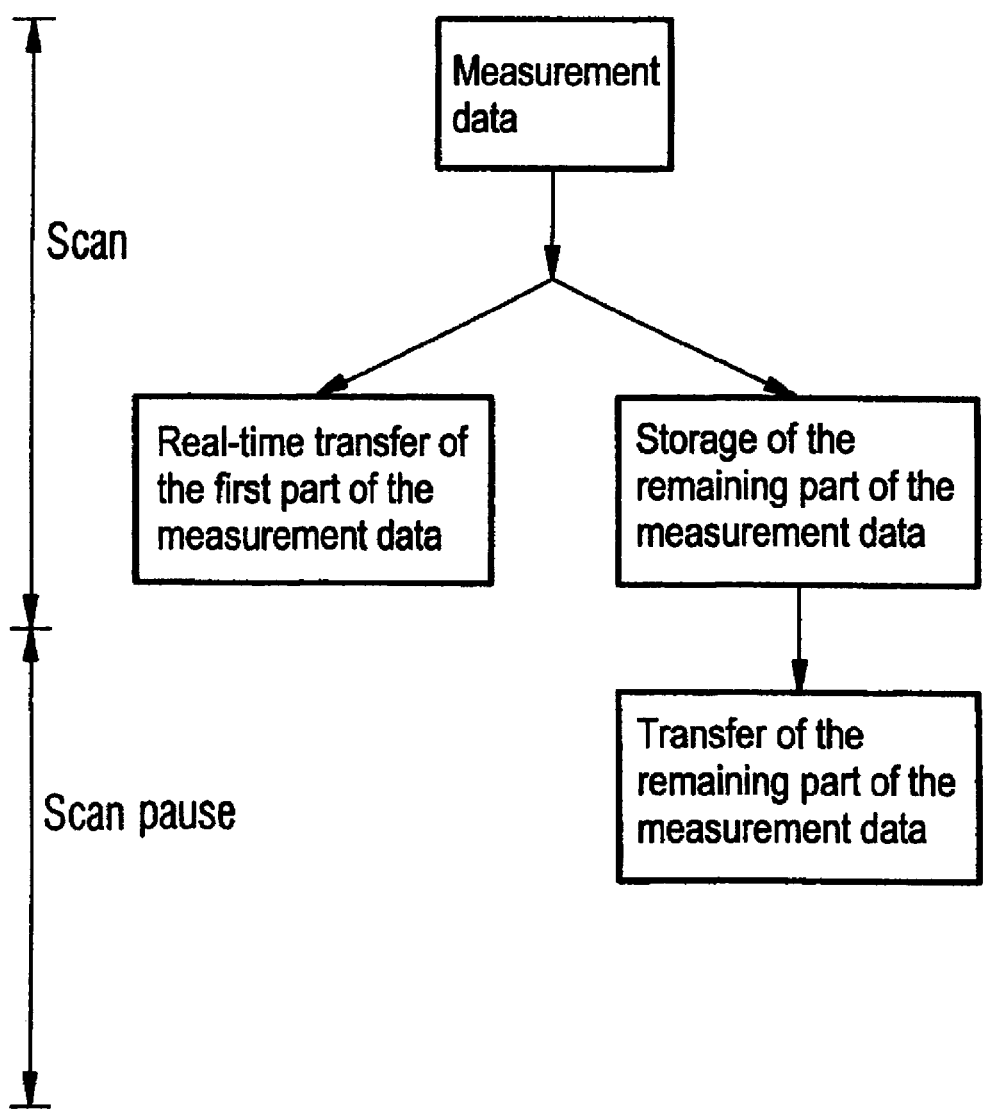

MULTI-SLICE COMPUTER TOMOGRAPHY SYSTEM WITH DATA TRANSFER SYSTEM WITH REDUCED TRANSFER BANDWIDTH

BACKGROUND OF THE INVENTION

1. Field of the Invention

The present invention concerns a computed tomography (CT) system of the type having a stationary part and a part rotatable around an examination axis that carries at least one x-ray source, a detector unit opposite the x-ray source and a data acquisition unit connected with the detector unit, and a data transfer device for transfer of measurement data (acquired with the data acquisition unit) to an image reconstruction device connected with the stationary part is fashioned between the stationary part and the rotatable part. The present invention also concerns a method for operation of such a CT system.

2. Description of the Prior Art

In multi-slice CT systems, detector arrays with a number of detector rows are used that can be simultaneously exposed by an x-ray beam that conically expands in the direction of the examination axis, what is known as the z-axis. In this manner, a number of slices of the examination subject can be simultaneously acquired with a complete rotation of the rotatable part. This offers a better continuity from slice to slice, as well as the possibility of a noticeably faster data acquisition, as is of great advantage for prevention of movement artifacts, particularly in heart examinations. An increasing need therefore exists for CT systems with which thinner slices of a volume region can be acquired in the same measurement time to increase the resolution, but with which the measurement time can be shortened for the acquisition of a specific volume region.

To meet this need, CT systems with larger, laminar detector units have been proposed that, due to the increase of simultaneously-acquirable examination regions, are designated as volume CT systems. The laminar detector units have a very large number of detector rows (for example in the range between 256 and 1024 detector rows) that can be simultaneously exposed by an x-ray beam that conically expands in the z-direction. The acquisition of a large volume region with only a single complete rotation of the rotatable part around the patient is possible in this manner. However, the large number of detector rows in such a CT system leads to an enormous increase of the measurement data, accumulating per unit of time, which are acquired by the data acquisition unit and must be transmitted to the stationary image reconstruction unit. During typical rotation speeds of the rotating part, such a detector unit generates measurement data with a data rate in the range of 20 to 80 Gbps. However, the presently used data transfer devices are not fashioned for the transfer of such high data rates from the rotating part to the stationary part of the CT system.

The data transfer devices present in multi-slice CT systems transfer the measurement data acquired by the data acquisition unit to the stationary part (with which the image reconstruction unit is connected) in real time via capacitive or optical transfer devices employing slip rings. A single such slip ring enables a data transfer rate of approximately 2.5 Gbps. For the transfer of higher data rates, a number of slip rings must be arranged in parallel on the rotatable and/or stationary part. For a planar detector array for simultaneous acquisition of 256 to 1024 slices, this requires a parallel arrangement of 8 to 32 slip rings. This solution, however, occupies space within the CT gantry and the examination region that is already scarce, and incurs high costs. Improved technologies for data transfer with high data rates (and the costs associated therewith) have not proven to be practical.

SUMMARY OF THE INVENTION

An object of the present invention is to provide a CT system as well as a method for the operation thereof with which the data quantities accumulating in the laminar detector units can be transferred to the stationary part without high costs.

This object is achieved by a computed tomography system as well as a method according to the invention.

The inventive computed tomography system has, in a known manner, a stationary part and a part rotatable around an examination axis (the z-axis) that carries at least one x-ray source, one detector unit opposite the x-ray source and a data acquisition unit connected with the detector unit. A data transfer device (for example using one or more optical or capacitive slip rings) for transfer of the measurement data acquired with the data acquisition unit to an image reconstruction device connected with the stationary part is disposed between the stationary part and the rotatable part. The inventive computer tomography system is characterized by the rotatable part having a storage unit, connected with the data acquisition unit, for buffering (caching) at least one part of the measurement data acquired with the data acquisition unit before transfer of that data. This enables operation of the CT system in which only one part of the measurement data accumulates during the measurement, i.e. during a scan or a rotation of the rotatable part, is transferred in real time to the stationary part via the data transfer device, and the remaining part is buffered (cached) in the storage unit and transferred at a later point in time.

The present invention is based on the recognition that the transfer bandwidth available in existing CT systems is only partially utilized during an examination of a patient. The complete transfer bandwidth is used only during the data acquisition for transfer of the acquired measurement data in real time. The data transfer system is not used at all during other times, for example during patient registration and preparation, the establishment of the scan regions or the image reconstruction and analysis. On average utilization of the data transfer bandwidth of a typical CT system is in the range of 10% of the maximum possible capacity.

The high-resolution image reconstruction in a multi-slice CT system is significantly slower than the data acquisition and data transfer. The transferred measurement data therefore must in any case be stored initially in the image reconstruction unit. The image reconstruction normally subsequently ensues off-line. This applies all the more in volume CT in which, due to the complicated reconstruction algorithms for conical x-ray beams and the significantly higher number of 800 to 3000 images per second, a distinctly longer time is necessary for the image reconstruction than with the present multi-slice CT systems (which can reconstruct less than 10 images per second given a conical x-ray beam).

In the inventive CT system with the buffer for buffering a part of the measurement data, that are then transferred only at a later point in time, for example immediately after the implementation of a scan, the existing transfer bandwidth can be better utilized. The inventive CT system enables the use of only one or a few slip rings for data transfer, even for the very large measurement data quantities that accumulate in volume CT. An interference or obstruction of the examination thus is not caused in the situations explained above.

In particular, it is that a sequential scan (i.e. a step-by-step shifting of the patient table from scan region to scan region), rather than a spiral scan, ensues in the implementation of volume CT. This is because of the large volume region that can be acquired with one rotation, in particular its large extent in the z-direction, which would require an impractically fast movement of the patient table for a spiral scan. However, the step-by-step shifting of the patient table in turn involves measurement pauses during which the remaining measurement data can be transferred at least in part. Should this time window not be sufficient, the remaining measurement data are transferred to the stationary part and the image reconstruction device after conclusion of the measurement data acquisition. A particular advantage of the inventive CT system as well as the inventive operating method is their compatibility with existing data transfer systems. Thus the same data transfer devices can be used as are already used in known multi-slice CT systems. The present invention requires only the retrofitting (with the storage unit as well as the associated data administration system) the electronics used on the rotatable part.

The storage unit preferably is dimensioned such that it can maximally store at least all measurement data accumulating during one complete rotation of the rotatable part in the measurement operation of the CT system. In specific applications, a single such rotation can already be sufficient in order to acquire the complete examination region. However, naturally it is advantageous to dimension the storage unit such that it also can accommodate the maximum acquirable measurement data quantities of a number of scans. The storage unit itself is fashioned as a fast RAM storage in an embodiment of the inventive CT system. However, the storage unit preferably has two storage levels, of which the first storage level is a fast buffer storage (in particular a fast RAM storage) and the second storage level is a permanent storage. The measurement data received from the data acquisition unit are thereby initially buffered in the first storage level and then transferred to the slower permanent storage. This permanent storage prevents the loss of the already-acquired data in the event of a power interruption. The permanent storage can be designed, for example, a flash memory, a flash disk module, as a compact flash card or a similar storage card, as a shock-resistant hard drive or as an IBM micro-hard drive. The permanent storage is preferably portable as a removable module on the rotatable part, such that given a failure of the CT system it can be removed without difficulty and inserted into a suitable acquisition interface for transfer of the data to the image reconstruction unit.

The inventive CT system preferably is provided with a laminar detector unit with at least 256 detector rows (lines) for simultaneous acquisition of 256 slices as is used for implementation of volume CT. The x-ray source as well as the collimator disposed in front of it is fashioned in the same manner for simultaneous exposure of all detector rows. On the other side, the data transfer device preferably is dimensioned only for the real-time transfer to the stationary part of a fraction of the measurement data quantity accumulating in the operation of the CT system. The data transfer device of the inventive CT system can be realized cost-effectively in this manner without limiting the operation of the CT system due to the limited data transfer rate.

In an embodiment of the inventive CT system and the associated method, a data administration system for the administration of the data storage is provided that can be fashioned as an independent unit or as a part of the data acquisition unit. This data administration system selects (from the measurement data received via the data acquisition unit) the measurement data of predetermined slices that are transferred in real time via the data transfer device. The remaining data are stored in the storage unit and transferred at a later point in time. This offers the possibility of the specification of specific slices, for example each nth slice, a real-time reconstruction and representation of these selected slices can be realized in the event that this is necessary for the respective application. The remaining measurement data are transferred after the measurement data acquisition and can serve to improve the spatial resolution of the reconstructed examination region.

DESCRIPTION OF THE DRAWINGS

FIG. 1 schematically illustrates an embodiment of the inventive CT system.

FIG. 2 shows an example for a laminar detector unit in schematic representation that can be used in the inventive CT system.

FIG. 3 illustrates an example for the workflow in the data acquisition and data transfer with the inventive CT system and method.

DESCRIPTION OF THE PREFERRED EMBODIMENTS

FIG. 1 schematically illustrates an example for the design of a volume CT system according to the present invention. An x-ray tube 1 attached to a rotatable part 11, known as the gantry, and emits a conical x-ray beam 2 whose aperture angle can be set in the x-direction and z-direction by a mechanically adjustable diaphragm 3. FIG. 1 shows a section perpendicular to the z-direction. The x-ray beam 2 penetrates a patient body 4 and strikes a planar detector unit 5.

In the present example, a detector unit 5 with 1024 detector rows is used with which 1024 individual slices can be acquired with a single scan. FIG. 2 schematically shows in plan view an example for the arrangement of the detector rows 14 and detector columns 15 of such a planar detector unit.

A data acquisition unit 6 disposed on the rotatable part 11 converts the analog measurement signals acquired by the detector elements of the detector unit 5 and delivers a serial stream of digital measurement data to a stationary image reconstruction unit 10 via a data transfer device formed by units 8 and 9. From the received measurement data, the stationary reconstruction unit 10 reconstructs the images of the individual slices of the examination region of the patient 4 acquired with the acquisition system (made up of x-ray tube 1 and detector unit 5).

The rotatable part 11 rotates continuously around the z-axis during the measurement. A slip ring transmission unit 8 on the rotatable part 11 and a slip ring reception unit 9 on the stationary part 12 of the CT system are served for data transfer during and after this rotation. Given a single rotation of the rotatable part, approximately 25 Gbits (3 Gbytes) of measurement data are generated within 0.3 seconds with the detector unit 5 (with 1024 detector rows).

Approximately thirty-two slip ring transfer units with respective transfer capacities of 2.5 Gbit/s would have to be arranged in parallel on the rotatable part and stationary part for a real-time transfer of these measurement data. In contrast to this, in the inventive CT system only one 2.5 Gbps (Gbit/s) slip ring transfer units 8, 9 with a single slip ring is used in order to transfer the same data quantity within the first 10 seconds after each scan. Only a fraction of the data is transferred in real time; the remaining part is transferred to the image reconstruction unit 10 after the implementation of the scan. For this purpose, a storage unit 7 that buffers the measurement data not transferred in real time during the measurement data acquisition period is disposed on the rotatable part 11. A data administration system 13 selects the accumulating data for storage and/or real-time transfer and supervises the later transfer of the stored data. FIG. 1 also exemplarily shows the partitioning of the storage unit 7 into a fast RAM storage 7a and a slower permanent storage 7b that—as indicated with the arrow—can be removed from the rotatable part 11 in order to be able to directly read out the data stored in the permanent storage 7b, for example by insertion into a suitable acquisition unit of the image reconstruction unit 10.

The stored measurement data are then transferred to the image reconstruction unit 10 with the available transfer rate only after the measurement data acquisition. This is illustrated again in the exemplarily workflow shown in FIG. 3. The measurement data accumulating during a scan are divided into two data quantities by the data administration system 13 that is indicated in FIG. 1 as part of the data acquisition unit 6. A first data quantity is transferred to the image reconstruction unit 10 in real time during the measurement data acquisition, a second, remaining part of the measurement data is buffered in the storage unit 7. After implementation of the scan or the measurement data acquisition, the remaining part is read out from the storage and likewise transferred to the image reconstruction unit 10. The first data can thereby be the data of predeterminable slices of the examination volume acquirable with the acquisition system in a single scan. For example, given a detector unit for 1024 slices each 32nd slice can be transferred in real time in this manner in order to obtain in this manner an image representation of the examination region during the measurement with lower spatial resolution.

The data administration system 13 can be configured, for example, for selection of the corresponding slices or measurement data via a control connection between the stationary part 12 and the rotatable part 11 as it is already present in conventional computer tomograph systems. Measurement data of higher priority that are transferred in real time thus can be determined by this configuration, while the remaining measurement data are respectively sent to the image reconstruction unit 10 in corresponding measurement pauses with lower priority.

Although modifications and changes may be suggested by those skilled in the art, it is the intention of the inventor to embody within the patent warranted hereon all changes and modifications as reasonably and properly come within the scope of his contribution to the art.

I claim:

1. A computed tomography system comprising:
   a stationary part;
   a rotatable part, mounted for rotation around an examination axis relative to said stationary part;
   an x-ray source mounted on said rotatable part;
   a radiation detector unit mounted on said rotatable part opposite said x-ray source;
   a data acquisition unit mounted on said rotatable part and connected to said radiation detector unit for receiving radiation attenuation data from said radiation detector unit;
   an image reconstruction device that is stationary with respect to said rotatable part;
   a data transfer device disposed between said data acquisition unit and said image reconstruction device for transferring said attenuation data from said data acquisition unit to said image reconstruction device;
   a storage unit connected to said data acquisition unit for buffering at least a portion of said attenuation data received by said data acquisition unit before said attenuation data are transferred to said image reconstruction device; and
   said data acquisition unit comprising a data administration system for transferring a first portion of said attenuation data directly to said data transfer device in real time and for storing a second part of said attenuation data in said storage unit for subsequent transfer to said image reconstruction device via said data transfer device.

2. A computed tomography system as claimed in claim 1 wherein said data transfer device operates with a transfer rate that does not allow all of said attenuation data that accumulate during an attenuation data measurement event to be transferred in real time to said image reconstruction device.

3. A computed tomography system as claimed in claim 1 wherein said storage unit has a storage capacity allowing storage of all attenuation data that accumulate during at least one complete rotation of said rotatable part.

4. A computed tomography system as claimed in claim 1 wherein said x-ray source emits a conical x-ray beam, and wherein said radiation detector unit comprises a multi-slice detector array that is completely exposed by said conical x-ray beam.

5. A computed tomography system as claimed in claim 1 wherein said data transmission system causes said second portion of said attenuation data to be transferred as soon as said data transfer device has a free data transfer capacity.

6. A computed tomography system as claimed in claim 1 wherein said data administration system selects said first portion of said attenuation data dependent on predetermined priorities.

7. A computed tomography system as claimed in claim 6 wherein said x-ray source emits a conical x-ray beam and wherein said radiation detector unit comprises a multi-slice detector array that is completely exposed by said conical x-ray beam, and wherein said data administration system selects attenuation data from predetermined slices detected by said multi-slice detected array as said first portion of said attenuation data.

8. A computed tomography system as claimed in claim 1 wherein said storage unit comprises a RAM storage for fast storage and a permanent storage into which attenuation data stored in said RAM storage are transferred.

9. A computed tomography system as claimed in claim 8 wherein said permanent storage comprises a portable, removable storage module.

10. A method for operating a computed tomography system comprising the steps of:
   acquiring a quantity of attenuation data from a subject during a data acquisition event with a rotating data acquisition unit;
   electronically transferring a first portion of said attenuation data in real time during said data acquisition event from said data acquisition unit to an image reconstruction device located remote from said data acquisition unit and being stationary with respect to said data acquisition unit;

buffering a second portion of said attenuation data in a storage unit, connected to and rotating with said data acquisition unit, during said data measurement event; and transferring said second portion of said attenuation data from said storage unit to said image reconstruction device at a point in time following storage of said second portion in said storage unit to make a complete user-accessible dataset, comprising said first portion of said attenuation data and said second portion of said attenuation data, available at said image reconstruction device that allows reconstruction of an image of the subject therefrom.

11. A method as claimed in claim 10 wherein said attenuation data represent data from respective slices of an examination subject, and comprising transferring only data from predetermined slices, as said first portion of said attenuation data, in real time.

12. A method as claimed in claim 10 comprising initially buffering said second portion of said attenuation data in a RAM storage of said storage unit, and transferring said second portion to a permanent storage of said storage unit.

13. A method as claimed in claim 10 wherein said data measurement event comprises data acquisition pauses, and transferring said second portion of said attenuation data from said storage unit to said image reconstruction device during said measurement pauses.

* * * * *